United States Patent [19]

Tamura et al.

[11] E Patent Number: Re. 32,153

[45] Reissued Date of Patent: May 20, 1986

[54] HIGHLY THERMOSTABLE GLUCOAMYLASEAND PROCESS FOR ITS PRODUCTION

[75] Inventors: Masaki Tamura, Kamakura; Mizuho Shimizu, Hino; Minoru Tago, Tokyo, all of Japan

[73] Assignee: CPC International Inc., Englewood Cliffs, N.J.

[21] Appl. No.: 761,930

[22] Filed: Aug. 2, 1985

Related U.S. Patent Documents

Reissue of:

[64] Patent No.: 4,247,637
Issued: Jan. 27, 1981
Appl. No.: 55,723
Filed: Jul. 9, 1979

[30] Foreign Application Priority Data

Sep. 1, 1978 [JP] Japan ..... 53-106354

[51] Int. Cl.[4] ..... C12P 19/20; C12N 9/34; C12N 1/645

[52] U.S. Cl. ..... 435/96; 435/205; 435/911

[58] Field of Search ..... 435/96, 205, 911

[56] References Cited

FOREIGN PATENT DOCUMENTS 537513 3/1978 Japan .
987343 3/1965 United Kingdom .
1470325 4/1977 United Kingdom .

OTHER PUBLICATIONS

Taylor, et al., "Some Properties of a Glucoamylase Produced by the Thermophilic Fungus *Humicola lanuginosa*", *Carbohydrate Research*, 61, 301–308 (1978).

Subrahmanyam, et al., "Amyloglucosidase Production by *Torula thermophilia*", *Indian J. Biol.*, 15, 495–496 (1977).

Derwert Abstract of Kanno et al., Japanese Patent Sho 53–7513.

*Primary Examiner*—Lionel M. Shapiro

[57] ABSTRACT

Process for the production of a thermostable glucoamylase by a strain of Talaromyces and the glucoamylase produced thereby.

8 Claims, 3 Drawing Figures

EFFECT OF pH ON RELATIVE ACTIVITY AT 60°C

EFFECT OF TEMPERATURE ON RELATIVE ACTIVITY AT pH 6.0

COMPARISON OF THE THERMOSTABILITIES OF THIS ENZIME AND THE CONVENTIONAL GLUCOAMYLASES WITHOUT SUBSTRATE AT 70 °C

HIGHLY THERMOSTABLE GLUCOAMYLASEAND PROCESS FOR ITS PRODUCTION

Matter enclosed in heavy brackets [ ] appears in the original patent but forms no part of this reissue specification; matter printed in italics indicates the additions made by reissue.

BACKGROUND OF THE INVENTION

At present, batch processes are applied to the production of dextrose by saccharification of starch hydrolyzates with a glucoamylase. Many of the commercially-available glucoamylase enzymes produced today are derived from microorganisms of the genera Rhizopus and Aspergillus. When these enzymes are used to produce dextrose, they are generally reacted at 55° C. to 60° C. for 2 to 4 days. If glucoamylase can be immobilized and the saccharification can be conducted continuously through a column, the reaction time is reduced and no large reaction tank is necessary thereby saving labor and energy. Glucoamylase enzymes produced by Rhizopus and Aspergillus can be immobilized by ion exchange processes, physical adsorption, covalent bonding, gel entrapment, etc. Any glucoamylase enzymes immoblized by any of these processes are, however, inactivated when used at above 50° C.

An article by Marsh, D. R., Lee, Y. Y., and Tsao, G. T., Biotech. Bioeng. 15, 483 (1973) reported that immobilized glucoamylase enzymes were stable for a considerably long period of time when they were used at below 50° C., but this process is not commercially feasible because of the danger of microbial contamination.

Therefore, the development of an immobilized glucoamylase stable at temperatures above 50° C. is necessary for continuous saccharification in commercial operations.

To achieve this, a glucoamylase having remarkably higher thermostability than those of conventional ones must be developed.

SUMMARY OF THE INVENTION

A microbial strain has been discovered belonging to the genus Talaromyces which produces a glucoamylase having an optimum reaction temperature of 75° C. and characterized as being capable of retaining at least about 90% of its initial glucoamylase activity when held at 70° C. and pH 4.5 for 10 minutes. This invention includes the method for the production of this glucoamylase wherein a microorganism of the genus Talaromyces, which produces the glucoamylase, is cultured in a medium and the enzyme is recovered from the culture broth.

DETAILED DESCRIPTION OF THE INVENTION

The properties of the novel thermostable glucoamylase of the present invention are presented in detail, and their properties are contrasted with those of the previously-known glucoamylases.

The term "D.E." is an abbreviation for "dextrose equivalent", and these terms are used interchangeably to refer to the reducing sugar content of a material calculated as dextrose and expressed as percent of total solids.

The term "starch hydrolyzate" is used in a general way to refer to a syrup or dry product that is made by the partial hydrolysis of starch. Such a product may be made by acid or enzymic hydrolysis.

The term "liquefied starch" is used to refer to a low D.E. (D.E. from about 2 to about 20) startch hydrolyzate.

1. Activity and Substrate Specificity

This enzyme hydrolyzes starch, soluble starch, amylose, amylopectin, glycogen, etc., into dextrose. When the substrate concentration is 1%, the yield of dextrose is 100% and the optical rotation of the formed dextrose is positive; hence this enzyme is a glucoamylase.

2. Optimum pH and Stable pH Range

Figure 1:
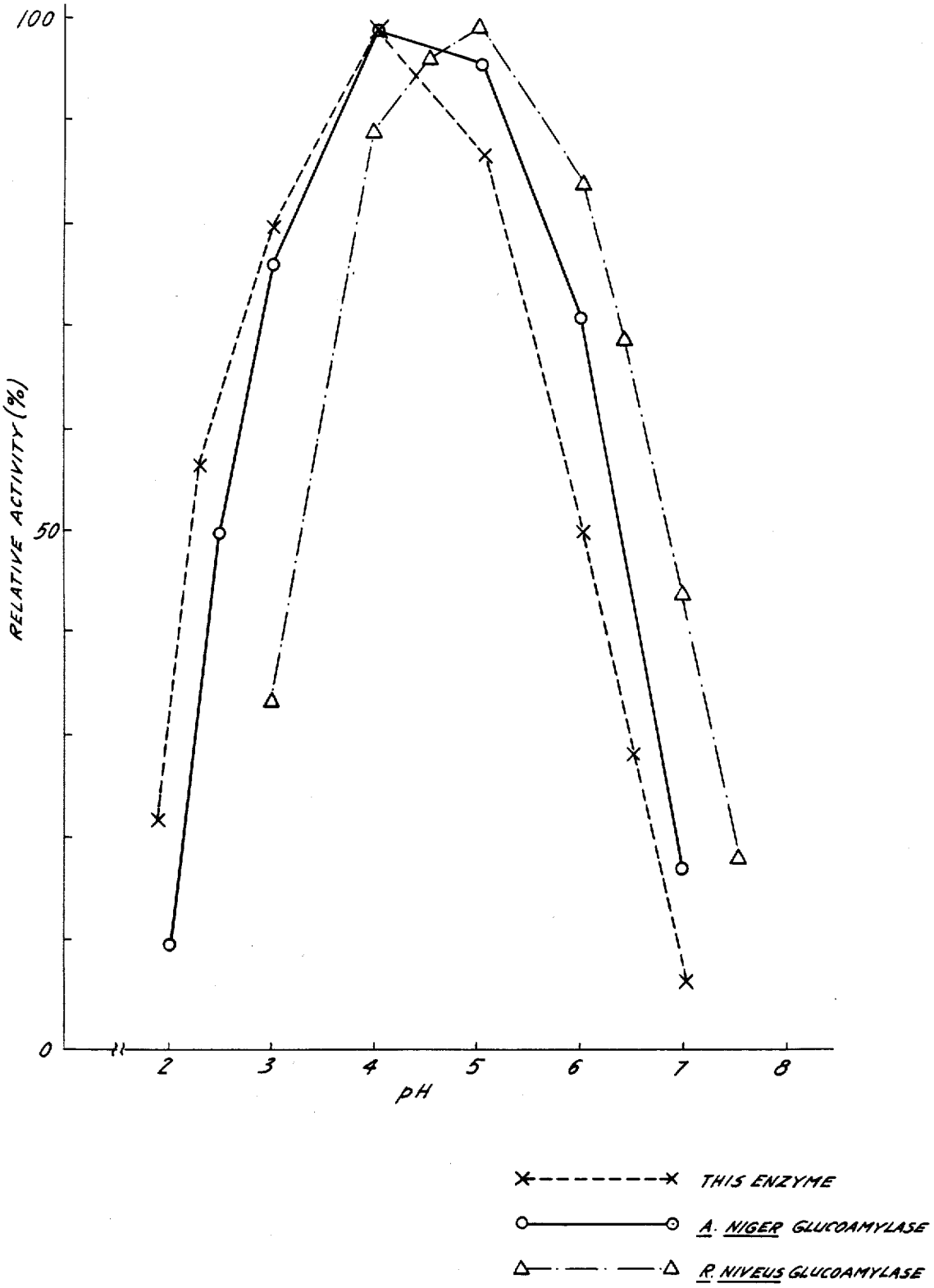
FIG. 1 shows the relationship between the pH and the enzyme activity in the cases of the enzyme of the present invention and the conventional glucoamylases produced by R. niveus and A. niger microorganisms.

FIG. 1 shows the relationship between the relative enzyme activity and the pH in comparison with those of the glucoamylases produced by Rhizopus and Aspergillus. As shown in the figure, the optimum pH of this enzyme at 60° C. is 4.0 and those of the glucoamylases produced by Rhizopus and Aspergillus are 5.0 and 4.0, respectively. This enzyme is most stable at pHs between 3 to 5, but no inactivation was found to occur when it was held at room temperature and a pH of between 2 to 9 for 24 hours.

3. Determination of Enzymatic Activity

A 0.5 ml aliquot of a diluted enzyme solution is added to 0.5 ml of a 2% maltodextrin (D.E. about 10) solution in 0.1 M acetate buffer (pH 4.5) and this is reacted at 60° C. for exactly 10 minutes. After 10 minutes, the enzyme reaction is terminated by heating in a boiling water bath for 5 minutes. The extrose formed is determined using the glucose oxidase method. The enzyme amount which is capable of producing 1 micromole of dextrose per minute is defined as 1 enzyme unit.

4. Range of Reaction Temperature

Figure 2:
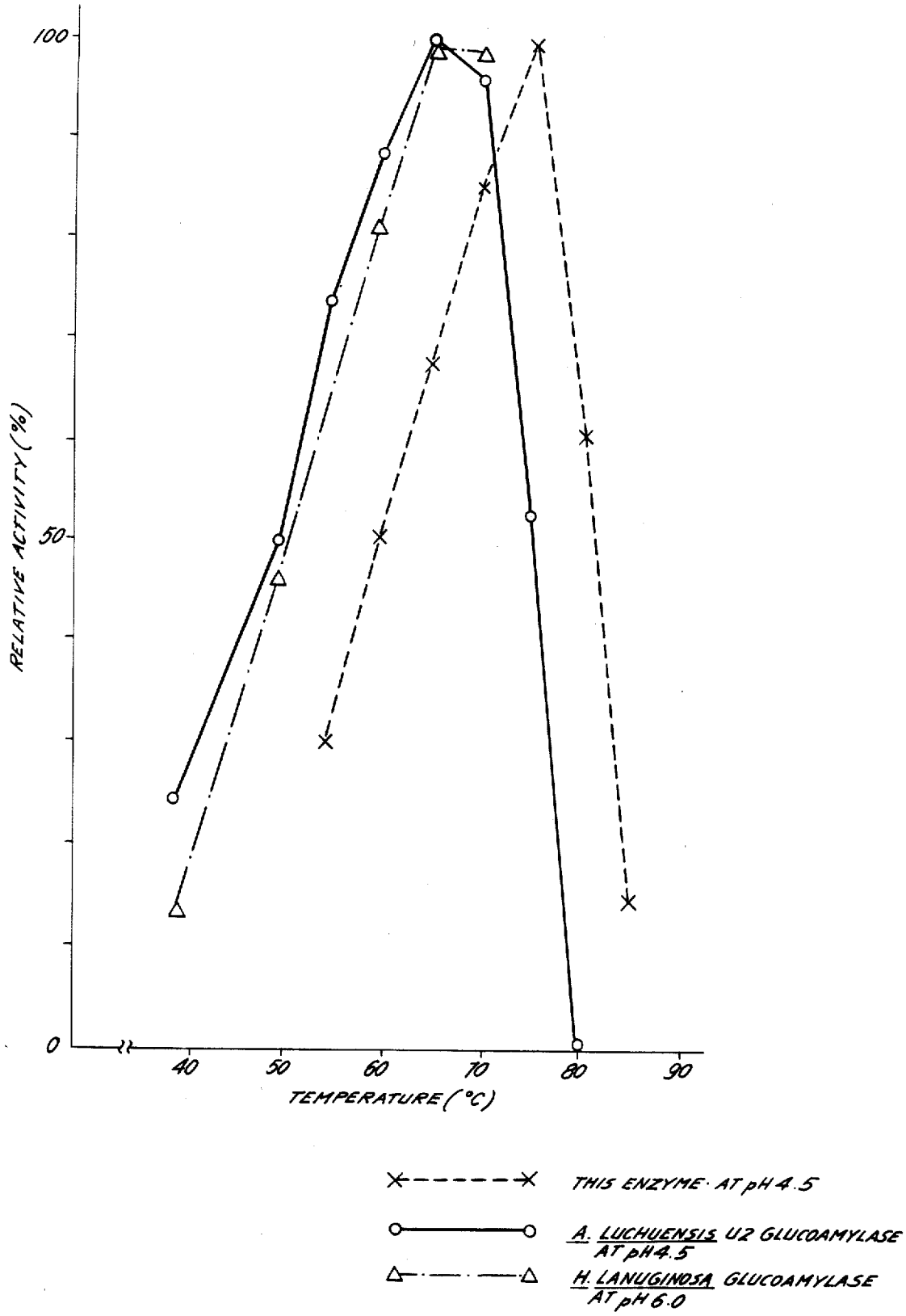
FIG. 2 shows the relationship between the temperature and the enzyme activity in the cases of the present enzyme and the glucoamylases from A. luchuensis and H. lanuginosa.

FIG. 2 shows the relationship between the relative enzymatic activity and the reaction temperature in comparison with that of the glucoamylase produced by Aspergillus luchuenis U2 (Public Notice of Japanese Patent Sho No. 53-7513) and also that the glucoamylase produced by Humicola lanuginosa (Carbohydrate Research, 61 301, 1978), which are the most thermostable glucoamylases known to date. As shown in the figure, the optimum reaction temperature of this enzyme is 75° C., which is 10° C. higher than that of Aspergillus luchuensis and Humicola lanuginosa.

5. Inactivation Due to pH and Temperature Conditions.

Figure 3:
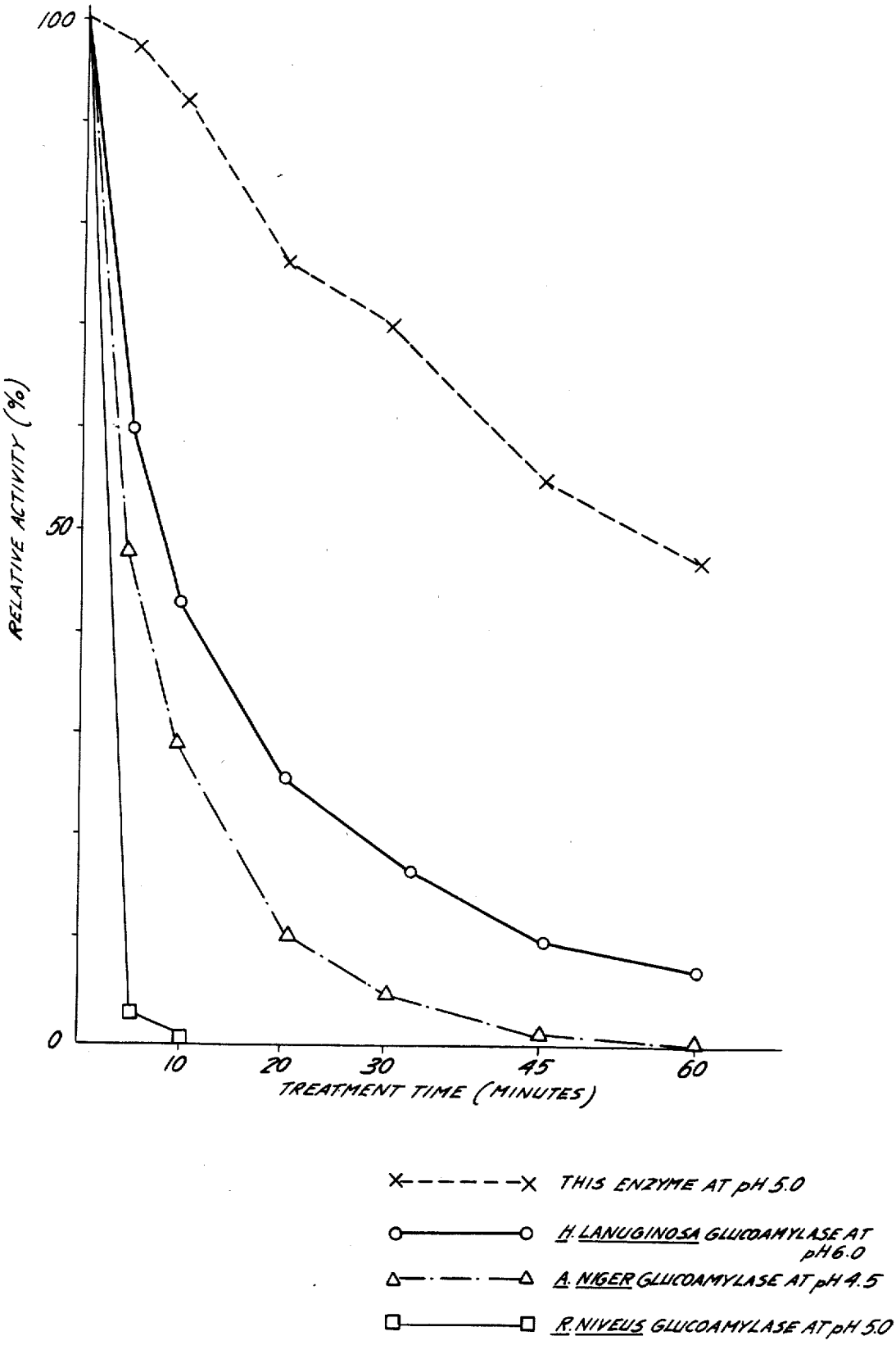
FIG. 3 provides a comparison of the present enzyme and the glucoamylases produced by the H. lanuginosa, A. niger and R. niveus microorganisms in terms of their relative thermostabilities.

This enzyme is completely inactivated by heating at 70° C. and at pHs less than 2 or above 8 for 1 hour. FIG. 3 shows the inactivation curve of this enzyme in comparison with those of the glucoamylases produced by Humicola lanuginosa, Aspergillus niger and Rhizopus niveus. Namely, the figure shows the inactivation curves of these four gluoamylases when they were treated at 70° C. and their optimum pHs for stability.

As shown in the figure, the present enzyme has a remarkably higher thermostability than the known glucoamylases, showing 92.5% residual activity after heating at 70° C. for 10 minutes and 48% residual activity even after heating for 1 hour. This fact indicates that this glucoamylase is significantly more thermostable than the known glucoamylases.

6. Inhibition, Activation and Stabilization

This enzyme does not require any activating nor stabilizing agents. It is inhibited by such metal salts as mercury bichloride.

7. Purification Process

This enzyme can be purified through salting-out with an inorganic salt, fractionation with an organic solvent, treatment with active clay, various chromatographic methods, etc., and combinations thereof. An embodiment of the purification process is described in the example.

When the purified enzyme was analyzed by disc electrophoresis in accordance with the Davis method: Ann New York Acad. Sci. 121, 321 (1964), it migrated toward the cathode at pH 8.8 and showed a single band.

8. Molecular Weight

The molecular weight of the present enzyme was investigated using a Sephadex G-150 column in accordance with the procedure of Andrews, P., Biochem. J. 96, 595 (1965). The results indicated that this enzyme's molecular weight is about 31,000.

Next, the points of difference between the present enzyme and the conventionally-known glucoamylases will be presented, and an explanation will be made of the reasons that this enzyme is to be considered a new enzyme having high thermostability.

Table I shows the optimum reaction pH, the optimum reaction temperature and the molecular weight of the present enzyme in comparison with those of several known glucoamylases. The optimum reaction temperature of the present enzyme is 75° C., which is 5° to 15° C. higher than those of the known glucoamylases. The molecular weight of the present enzyme is significantly smaller than those of the known glucoamylases.

TABLE I

COMPARISON OF VARIOUS GLUCOAMYLASES IN TERMS OF OPTIMUM pH, OPTIMUM TEMPERATURE AND MOLECULAR WEIGHT

| Glucoamylase | Optimum pH[a] | Optimum Temp. °C.[a] | Molecular Weight[a] |
|---|---|---|---|
| Present Enzyme (Talaromyces) | 4.0* | 75* | 31,000* |
| *Humicola lanuginosa*[b] | 6.5 | 65 | — |
| *Aspergillus luchensis*[c] | 4.0 | 65 | — |
| *Aspergillus niger* | 4.5* | 70* | 97,000[d] |
| Rhizopus sp. | 5.0* | 60* | 70,000[e] |
| Endomyces sp.[f] | 5.0 | 60 | 64,000 |
| *Trichoderma viride*[g] | 5.0 | 60 | 75,000 |
| *Cephalosporium cherticola*[h] | 5.4 | 60 | 69,000 |

[a]All values except those marked with an asterisk (*) were taken from the references.
[b]P. M. Taylor et. al.: Carbohydrate Research 61,301 (1978).
[c]T. Kanno et. al.: Public Notice of Japanese Patent Sho 53 (1978)-7513.
[d]J. H. Pazur, et. al.: J. Biol Chem. 237, 1002 (1962).
[e]Hiromi et al.: Biochem Biophys. Acta 302,632 (1973).
[f]Hattori et. al.: Agr. Biol. Chem 25,895 (1961).
[g]Okada: J. Jap. Soc. Starch Sci. 21,282 (1974).
[h]H. Urbanek: Appl. Microbiol 30, 163 (1975).

FIG. 3 shows the inactivation curve of the present enzyme in comparison with those of the glucoamylases from Humicola lanuginosa, Aspergillus niger and Rhizopus niveus. These were heated at 70° C. at the most stable pH for each enzyme. As shown in the figure, the inactivation of the present enzyme is significantly slower than that of the other glucoamylases.

On the basis of the above facts, it can be concluded that the glucoamylase produced by the method of the present invention is a new thermophilic glucoamylase which has been totally unknown to date.

An explanation will now be made of the method for the production of the present enzyme.

As a desirable example of the glucoamylase-producing microorganism to be used in the present invention, there is strain G45-632, which was isolated from the soil by the present inventors. The microbiological characteristics of the present strain will be described below.

The morphological properties of the present strain were determined in accordance with the methods described by the researchers listed below:

Cooney, D. G. and Emerson, R. THERMOPHILIC FUNGI. W. H. Freeman and Company, San Francisco & London. 1964.

Raper, K. B. and Thom. C. A MANUAL OF PENICILLIA. Hafner Publishing Company, New York and London (1968).

Awao, T. and Mitsugi, K. Trans. Mycol. Soc. Japan 14, 145–160 (1973).

Minoura, K., Yokoe, M., Kizima, T., Nehira, T. Trans. Mycol. Soc. Japan 14, 352–361 (1973).

9. Morphological Properties of Strain G45-632

The present strain was cultured on two kinds of media in Petri dishes. The following sections present the morphological characteristics which were observed for isolated colonies.

(a) Potato Dextrose Agar Medium

When incubated at 40° C. for 3 days, the colonies are circular with a diameter of 6 to 7 cm. The vegetative hyphae are colorless. They grow thinly in the peripheral region of the colonies but become fluccose in the center with a thickness of 1 to 2 mm and have numerous conidia. They are grayish white with slightly green cleistothecia of less than 0.3 mm diameter lying randomly in the central and peripheral parts of the colony.

The bottom of the colonies is yellowish brown but the part which forms the cleistothecia is reddish brown, which secretes a yellowish brown pigment. The vegetative hyphae are 2 to 4.5μ in width and have septa. They consist of branched fibers from which conidiophores having septa protrude. The conidiophores have a smooth surface and are 30 to 2,000μ×2 to 3μ in size; the longer ones are often randomly branched.

The formation of the conidia is very irregular, sometimes sprouting directly from the top of the conidiophores and sometimes sprouting from the top of 1 to 4 phialides. Sometimes the phialides are double. The phialides are 10 to 15μ×2 to 3.5μ in size and have swollen bottoms.

The conidia run in a row, sometimes of more than 10 units. They are oval or long oval with a smooth surface, and are 5×3μ or less in size, having a brownish color under transparent light.

The ascocarps are spherical or elliptically spherical, being less than 300μ in diameter. The asci have no ascus-wall and are 10×8μ in size. The ascospores are yellowish and are 3 to 4μ in size, circular from the upper view but an equational furrow is visible in side view.

(b) Yeast Extract Starch Agar Medium

| | Percent |
|---|---|
| Difco Yeast Extract | 0.4 |
| Soluble Starch | 1.5 |
| $K_2HPO_4$ | 0.1 |
| $MgSO_4.7H_2O$ | 0.05 |
| Agar | 2 |

When inubated at 40° C. for 3 days, the colonies are circular with a diameter of 6 to 7 cm. The colonies are floccose and 1 to 2 mm in thickness. Young colonies are white but they gradually become a grayish white slightly green color. In parallel with this, numerous conidia are formed and the surface becomes powdery. The bottom of the colonies is reddish brown at the initial stage of growth, but gradually becomes dark brown and secretes a dark brownish pigment into the medium. On this culturing medium, no ascocarps are formed.

10. Physiological Properties of Strain G45-632

(a) Growth Temperature

This strain is capable of growth over a temperature range of 25° to 50° C., but it does not grow at 55° C. and the optimum growth temperature is in the vicinity of 40° C.

(b) Growth pH

This strain is capable of growth over a pH range of 3 to 9 but its optimum growth pH is between 6 and 7.

(c) Carbon Source

This strain is capable of assimilating such carbon sources as dextrose, fructose, [glactose] *galactose*, mannose, sucrose, maltose and starch.

Based on the above microbiological findings and the description in "Thermophilic Fungi" (D. G. Cooney and R. Emerson), and "Trans. Mycol. Soc. Japan, 14" (T. Awao and K. Mitsugi), Strain 45-632 was identified as Talaromyces duponti. *Further research indicated that this strain should be classified as Talaromyces leycettanus.*

The Talaromyces [duponti] *leycettanus* strain G45-632 is being stored at the Fermentation Research Institute, Agency of Industrial Science & Technology, Chiba City, Japan, as Deposit No. 4566.

The strain, Talaromyces [duponti] *leycettanus* G45-632, is one of the embodiments of the microorganism used in this invention and any microorganism belonging to genus Talaromyces which is capable of producing the above-mentioned novel thermophilic glucoamylase can be employed as well as the strain G45-632 and its mutant strains.

Regarding the cultivation of the microorganisms to be employed in the present invention, the general knowledge and techniques used in the culture of molds are applicable.

Namely, as the nutritional source medium, it is possible to employ the media which are used for the culture of ordinary molds. For example, various starches, starch hydrolyzates, corn meal, wheat flour, molasses, etc., can be employed as the carbon source, while peptone, defatted cottonseed meal, meat extract, yeast extract, casein, corn steep liquor, malt extract, soybean meal, skim milk, inorganic ammonium salts, inorganic nitrates, etc., can be employed as the nitrogen source. As the inorganic salts, it is possible to employ calcium chloride, magnesium sulfate, phosphate, sodium chloride, potassium chloride, etc. Furthermore, these carbon sources, nitrogen sources and inorganic salts can be used either singly or in appropriate combinations. In addition, when it is desired to promote the growth of the microorganism and bring about an increase in its enzyme production, it is possible to employ trace amounts of metallic salts, vitamins, amino acids, etc.

The culture conditions usually employed for molds are also applicable to the cultivation of this microorganism. Namely, in liquid culture, when this microorganism is cultured for 3 to 10 days at pH 5 to 8 and 30° C. to 45° C., the enzyme of the present invention is accumulated in the culture broth. Solid culture is also possible by using solid materials such as bran.

In the case of liquid culture, the mycelia are removed by any of the well-known methods such as filtration; then the filtrate can be concentrated under reduced pressure, or the enzyme can be salted out with the other proteins by adding inorganic salts such as ammonium sulfate, or the enzyme can be precipitated by the addition of an organic solvent such as acetone or isopropanol.

In the case of solid culture, the enzyme is first extracted from the cultured material by the use of water or a buffer solution. Then, as in the case of liquid culture, it is possible to obtain the enzyme in a concentrated form.

The crude preparations of this new thermophilic glucoamylase thus obtained can be purified in accordance with the method described in the example.

This new thermophilic glucoamylase of the present invention can be used for saccharification in the process for production of dextrose from starch.

Especially, if this glucoamylase is immobilized and continuous saccharification is carried out using the immobilized glucoamylase, it is so advantageous that an extended period of continuous saccharification at 60° to 65° C. is possible with a high yield.

The invention is further illustrated by reference to the following example in which all parts and percentages are by weight unless otherwise noted.

EXAMPLE

A liquid culture medium consisting of 5% soluble starch, 2% corn steep liquor, 0.5% cottonseed meal, 0.5% yeast extract, 0.1% dipotassium phosphate, 0.05% magnesium sulfate and 0.01 calcium chloride was adjusted to pH 7.0 and 100 ml of this was placed in a 500 ml Erlenmeyer flask. This medium was sterilized at 121° C. for 20 minutes, inoculated with Talaromyces [duponti] *leycettanus* strain G45-632 and incubated at 40° C. for 7 days on a shaker. After the culture was completed, the mycelia were removed from the culture fluid by filtration. The filtrate was found to contain 60 units of glucoamylase activity per milliliter.

The pH of this filtrate was adjusted to 6.0 with 2 N HCl, then active clay was added at 0.01 g/ml of the filtrate. After stirring for 15 minutes at room temperature, the active clay was removed by filtration. Two volumes of cold isopropanol was then added to the filtrate in order to precipitate the enzyme. The precipitate was centrifugally separated and dissolved in a small amount of Tris-HCl buffer (pH. 7.5). This enzyme-containing solution was then dialyzed against the same buffer for one night at 4° C. DEAE-cellulose, which had been equilibrated with the same buffer solution, was then added to the dialyzed enzyme solution and the enzyme was adsorbed to this carrier. The enzyme was eluted from it using a solution of the same buffer by linearly increasing its NaCl content from 0 to 0.5 M.

Then, two volumes of cold isopropanol was added to the eluate to precipitate the enzyme, and this precipitate was dissolved in a [0.005] *0.05* M Tris-HCl buffer (pH 5.5).

This enzyme solution was adsorbed to a CM cellulose column and the enzyme was eluted from it using a solution of the same buffer by linearly increasing its NaCl content from 0 to 0.5 M. The eluted fractions which contained the enzyme were pooled and the enzyme was precipitated with two volumes of isopropanol.

The precipitate was then dissolved in 0.05 M Tris-HCl buffer (pH 7.5), and this enzyme solution was adsorbed to a Sephadex G-150 column which had been equilibrated with the same buffer and the enzyme was eluted using the same buffer. The fractions showing the enzyme activity were pooled and the enzyme was precipitated by adding two volumes of isopropanol. The precipitate was then dissolved in a small amount of 0.05 M acetate buffer (pH 4.5). The purified enzyme solution thus prepared had a glucoamylase activity of 110 units/mg protein.

Then the above-mentioned enzyme solution in Tris-HCl buffer, which had been prepared by dissolving the precipitate with isopropanol after the active clay treatment, was immobilized by binding with AE cellulose using glutaraldehyde in accordance with the method of Glassmeyer et al., Biochemistry 10, 786 (1971). An immobilized enzyme having 2,000 units of enzymatic activity per gram of carrier was thus obtained. Three grams of this immobilized enzyme was packed in a column which was held at 60° C. and a saccharification test was carried out by continuously passing through said column at a rate of 0.5 bed volumes per hour, a 25% solution of starch hydrolyzate (D.E. about 10) which had been adjusted to pH 5.0 with 2 N HCl. The dextrose content of this saccharified solution was found to be 96.5% as a result of determination by high-performance liquid chromatography. After 1 month of continuous saccharification, no decline in the dextrose yield was found to have occurred.

For comparison, an A. niger glucoamylase, having the highest thermostability of the known glucoamylase, was also immobilized in accordance with the same procedures as above and a 25% solution of starch hydrolyzate (pH 4.5) was saccharified under the same conditions. The initial dextrose content was 95.5%, but this rapidly declined and became 85% after 2 weeks of saccharification.

We claim:

1. A process for producing a glucoamylase enzyme preparation which comprises culturing cells of a strain of Talaromyces [duponti] *leycettanus* in a nutrient medium and isolating the glucoamylase enzyme preparation from the culture medium.

2. The process of claim 1 wherein the strain of Talaromyces [duponti] *leycettanus* is Fermentation Research Institute, Deposit No. 4566.

3. The glucoamylase enzyme preparation, prepared according to the process of claim 2, which comprises a glucoamylase with a molecular weight of about 31,000 as determined by Sephadex G-150 column chromatography.

4. The glucoamylase enzyme preparation of claim 3 which has a maximum glucoamylase activity at about 75° C. as measured by a 10-minute reaction on a 2% maltodextrin solution at pH 4.5.

5. A glucoamylase enzyme preparation of claim 3 which retains at least about 90% of its initial glucoamylase activity when held at 70° C. for 10 minutes at pH 4.5.

6. In a continuous process for saccharifying a liquefied starch solution to a syrup of high dextrose content by contacting the liquefied starch at a temperature above about 60° C. with a glucoamylase enzyme preparation bound to an inert carrier, the improvement wherein said glucoamylase enzyme preparation is obtained by the process of claim 1 so that the continuous saccharification can be carried out for extended periods of time without decline in the dextrose yield.

7. The process of claim 6 wherein the glucoamylase is obtained from the strain of Talarmyces [duponti] *leycettanus*, Fermentation Research Institute, Deposit No. 4566.

8. The process of claim 7 wherein the saccharification is carried out at a pH of from about 4.0 to about 5.0.

* * * * *

UNITED STATES PATENT AND TRADEMARK OFFICE

CERTIFICATE OF CORRECTION

PATENT NO. : Re. 32,153

DATED : May 20, 1986

INVENTOR(S) : Masaki Tamura, et al.

It is certified that error appears in the above-identified patent and that said Letters Patent are hereby corrected as shown below:

Cover sheet, title, "GLUCOAMYLASEAND" should read --GLUCOAMYLASE AND--.
Column 1, line 3, "GLUCOAMYLASEAND" should read --GLUCOAMYLASE AND--.
Column 2, line 20, "startch" should read --starch--.
Column 2, line 45, "extrose" should read --dextrose--.
Column 2, line 53, "luchuenis" should read --luchuensis--.
Column 2, line 54, after "that" insert --of--.
Column 3, Table I, "Aspergillus luchensis" should read --Aspergillus luchuensis--.
Column 5, line 10, "inubated" should read --incubated--.
Column 7, line 42, "glucoamylase" should read --glucoamylases--.
Column 8, claim 7, "Talarmyces" should read --Talaromyces--.

Signed and Sealed this

Twenty-fifth Day of November, 1986

*Attest:*

DONALD J. QUIGG

*Attesting Officer* *Commissioner of Patents and Trademarks*